United States Patent [19]
Peyman et al.

[11] Patent Number: 5,405,355
[45] Date of Patent: Apr. 11, 1995

[54] METHOD OF RADIAL KERATOTOMY EMPLOYING A VIBRATING CUTTING BLADE

[75] Inventors: Gholam A. Peyman; Stephen A. Updegraff, both of New Orleans, La.

[73] Assignee: Vitrophage, Inc., Lyons, Ill.

[21] Appl. No.: 119,711

[22] Filed: Sep. 10, 1993

[51] Int. Cl.⁶ .................................. A61B 17/32
[52] U.S. Cl. .......................... 606/166; 606/169
[58] Field of Search .................... 606/166, 169

[56] References Cited

U.S. PATENT DOCUMENTS

| | | | |
|---|---|---|---|
| 4,188,952 | 2/1980 | Loschilov et al. | 606/169 |
| 4,619,259 | 10/1986 | Graybill et al. | 606/166 |
| 5,167,725 | 12/1992 | Clark et al. | 606/169 |
| 5,201,747 | 4/1993 | Mastel | 606/166 |
| 5,222,967 | 6/1993 | Casebeer et al. | 606/166 |
| 5,263,957 | 11/1993 | Davison | 606/167 |

FOREIGN PATENT DOCUMENTS 4090751  3/1992  Japan ............................. 606/169

OTHER PUBLICATIONS

Melles, G. R. and Binder, P. S. "Effects of Radial Keratotomy Incision Direction on Wound Depth", *Refract Corneal Surg*, 6:394, 1990.

Casebeer, J. C. and Shapiro, D. R. "Blade designed for improved safety and accuracy in radial keratotomy", *J Cataract Refract Surg*, 19:314, 1993.

Updegraff, S. A., McDonald, M. B. and Benerman, R., "Freeze Fracture Analysis of American, Russian and DuoTrak Incisions", ARVO Abstract, *Invest Opthalmol Vis Sci* 34 (Suppl): 801, 1993.

Berkeley, R. G., Sanders, D. R. and Piccolo, M. G., "Effect of Incision Direction on Radial Keratotomy Outcome", *J Cataract Refract Surg*, 17:819–824, 1991.

Primary Examiner—Stephen Pellegrino
Assistant Examiner—Nancy Mulcare
Attorney, Agent, or Firm—Wood, Herron & Evans

[57] ABSTRACT

Radial keratotomies can be performed by incising centrifugally. A vibrating diamond front cutting blade with a reverse cutting edge incises centrifugally to form a squared-off incision at the optical zone. The incision can be retraced if an enhancement is necessary with the vibrating blade without tearing the collagen or resulting in blade setting variability or variability due to corneal compression.

7 Claims, 1 Drawing Sheet

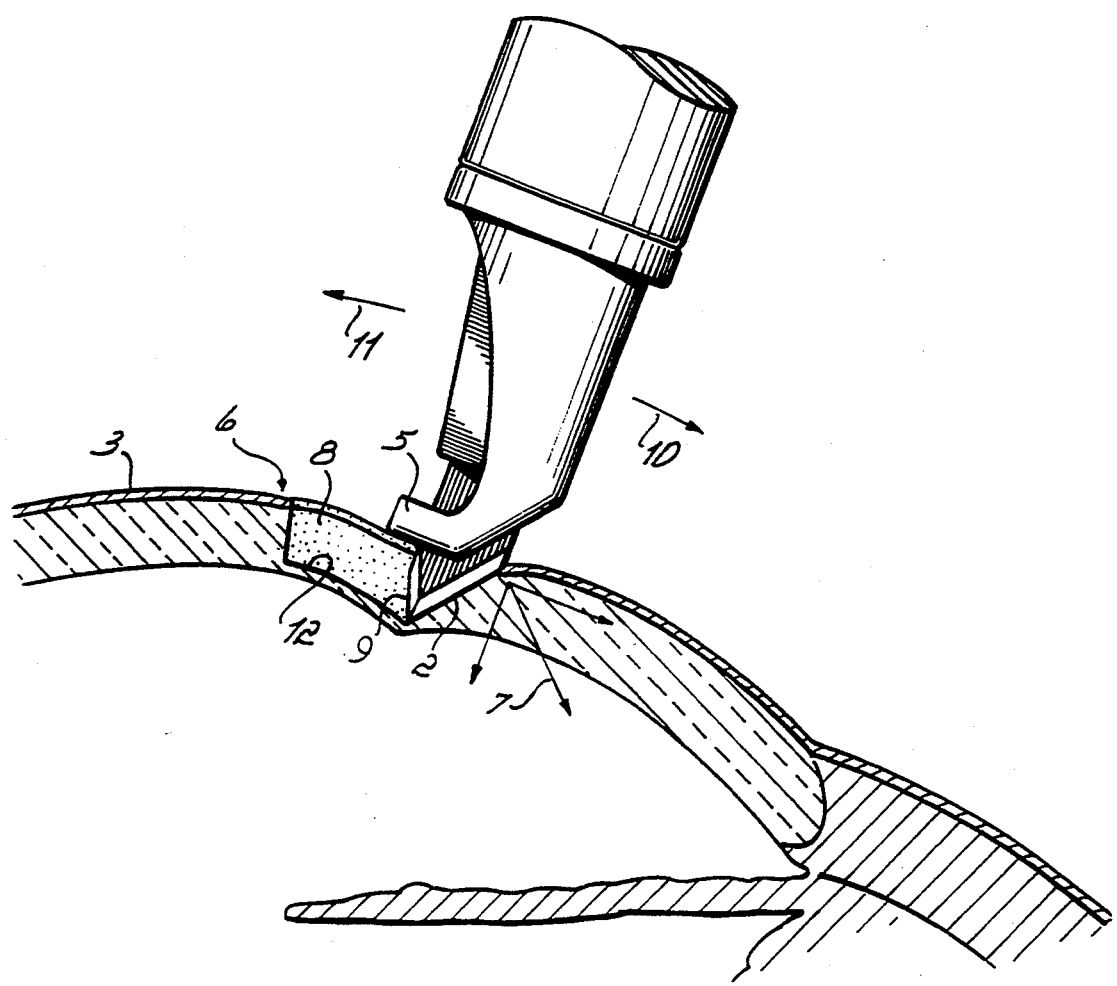

METHOD OF RADIAL KERATOTOMY EMPLOYING A VIBRATING CUTTING BLADE

FIELD OF THE INVENTION

The invention relates generally to a method of incisional keratotomy, and more particularly to a method of incisional keratotomy that employs a vibrating cutting blade for incising the cornea centrifugally to a maximal predictable depth.

BACKGROUND OF THE INVENTION

Surgeons performing radial keratotomy incise by utilizing one of two techniques, a centripetal incising technique or a centrifugal incising technique. Each technique has its own advantages and disadvantages.

Centripetal incisions are sometimes preferred because, while using the same blade setting, the centripetal incisions are deeper than centrifugal incisions. Melles, G. R. and Binder, P. S. "Effects of Radial Keratotomy Incision Direction on Wound Depth", Refract Corneal Surg, 6:394, 1990. The differences in incisional depth are due to the uphill vector forces associated with centripetal incisions. Centrifugal incisions are more shallow because of downhill vector forces directed out of the incision.

Centripetal incisions are retraceable and more uniform than centrifugal incisions. Most importantly, the centripetal incisions square off at the optical zone, thus forming a perpendicular architecture at the stopping point of the incision. Centrifugal incisions, on the other hand, round off at the optical zone. The physical characteristics of the cornea such as corneal compressibility, flexibility and intraocular pressure differ with the incisional depth and angle of the two incisional techniques.

Disadvantages of using the centripetal technique are known. A risk of extending centripetal incisions beyond the optical zone exists. Overextending the incision into the optical zone may overcorrect, as well as, reduce vision or cause glare. Such overextension resulting in these injuries may require a corneal transplant. Another disadvantage of the centripetal incision is difficulty in incising straight. Centrifugal incisions, however, are straighter than centripetal incisions.

A blade has been developed, i.e., System DuoTrak, for both centripetal and centrifugal incisions. Casebeer, J. C. and Shapiro, D. R. "Blade designed for improved safety and accuracy in radial keratotomy", J Cataract Refract Surg, 19:314, 1993. In the System DuoTrak, a front diamond blade first incises centrifugally with a full cutting edge. Then a centripetal incision retraces the centrifugal incision by employing a 200 u reverse straight cutting edge at its deepest aspect and a superficial blunt edge at the shallow aspect of the blade. The centrifugal incision is shallow, rounded off at the optical zone, and of irregular depth. The centripetal incision retraces the centrifugal incision correcting these deficits. The dull area of the reverse cutting edge guides the blade back over the centrifugal incision, preventing deviation from the centrifugal incision. The deeper aspect of the reverse cutting edge deeply and uniformly recuts the bottom of the centrifugal incision. When the reverse cutting edge reaches the optical zone, the deep reverse cutting edge stops because of the dull superficial edge of the blade. At this point, the reverse cutting edge squares off the optical zone. The reverse cutting edge will not incise past the optical zone because of the dull aspect of the blade.

Updegraff et al. have described the DuoTrak histology and optical zone structure. Updegraff, S. A., McDonald, M. B. and Benerman, R., "Freeze Fracture Analysis of American, Russian and DuoTrak Incisions", ARVO Abstract, Invest Opthalmol Vis Sci 34 (Suppl): 801, 1993. Updegraff et al. discovered that the centripetal incision made by the reverse cutting edge is irregularly displaced in relation to the centrifugal incision made by the diamond front cutting edge. The centripetal incision irregularly tears the collagen at the base of the first pass incision. Furthermore, the reverse cutting edge does not square off the optical zone. Instead, a portion of midstroma is unincised. Although ramifications of these problems are yet unknown, Updegraff et al. believe they do not duplicate the ideal configuration of the centripetal incision. Furthermore, the DuoTrak incisions may well be less repeatable than centripetal incisions.

BRIEF SUMMARY OF THE INVENTION

This invention is directed to a method of keratotomy comprising centrifugally incising the cornea. The method involves centrifugally incising the cornea with a vibrating cutting blade. By using a vibrating cutting blade, a maximal predictable incisional depth is obtained without irregularly tearing the corneal collagen and with less pressure to overcome compressibility forces of the cornea at the optical zone. This will create a square incision at the optical zone with one limbus directed pass.

Preferably, the blade is a diamond front cutting blade with a reverse cutting edge. This reverse-edge can be used for secondary enhancement procedures thus broadening the application of such a blade. The blade may be vibrated laterally or coaxially as well as ultrasonically. Most importantly, this invention provides a safe method for incising the cornea centrifugally while providing the efficacy of a centripetal incision.

Still other objects and advantages of the present invention will become readily apparent to those skilled in this art from the following detailed description wherein only the preferred embodiment of the invention is shown simply by way of illustration of the best mode contemplated of carrying out this invention. As will be realized, the invention is capable of other and different embodiments, and its several details are capable of modifications in various obvious respects, all without departing from the invention. Accordingly, the description is to be regarded as illustrative in nature and not as restrictive.

BRIEF DESCRIPTION OF THE DRAWING

FIG. 1 illustrates a portion of the cornea of the eye and a vibrating blade used for radial keratotomy according to this invention.

DETAILED DESCRIPTION OF THE INVENTION

FIG. 1 is an illustration of this invention. A diamond front cutting blade 2 with a 200-215 u reverse cutting edge 9, incises the cornea 3 during radial keratotomy. A vibrating blade handle 4 to which the blade attaches vibrates the blade laterally, coaxially or ultrasonically. Foot plates 5 are attached at the base of the blade handle. These foot plates 5 are parallel to the cornea and prevent too deep an incision by the blade.

The initial entry of the vibrating blade incises the optical zone 6. The vibrating blade overcomes vector forces 7 such as flexibility, compressibility and intraocular pressure forces of the cornea. The vibrating diamond front blade thus incises through the collagen 8 to a maximal predictable depth at the optical zone 6, without tearing the collagen 8 and without blade setting variability or variability due to corneal compression. Blade vibrations or oscillations on the order of about 100 to about 10,000 rate per minute may be employed. The 200–215 u reverse cutting edge 9 also incises the collagen 8 at the optical zone 6, squaring-off the incision 12.

The vibrating blade completes the centrifugal incision as shown by a directional arrow 10. A second enhancement incision as shown by a directional arrow 11 can then be made if the primary procedure leads to undercorrection. The second incision, as the first, does not irregularly tear the collagen, or result in blade setting variability or variability seen with corneal compression. The centrifugal incision eliminates the risk of overextending the incision beyond the optical zone while creating an incision with structural properties most similar to a centripetal incision. The proposed technique would obtain those features of centripetal incisions as shown by Berkeley, R. G., Sanders, D. R. and Piccolo, M. G., "Effect of Incision Direction on Radial Keratotomy Outcome" *J Cataract Refract Surg*, 17:819–824, 1991, namely, incision predictability and markedly reduced secondary procedures due to undercorrection, yet maintain the safety of a one pass incision toward the limbus. Less pressure exerted on the cornea to create such an incision will also keep intraocular pressure constant and thus prevent depth disparity between incisions in the same cornea.

What is claimed is:

1. A method of performing a radial keratotomy operation using a vibrating cutting blade having a tip and a foot plate spaced above said tip, which method comprises:

inserting said cutting blade into the optical zone of the cornea to the depth of said foot plate while vibrating said cutting blade; and centrifugally incising the cornea at the full depth of said foot plate while vibrating said cutting blade so as to form a corneal incision in a single pass having a constant fixed predictable depth for the length of Said pass without irregularly tearing the corneal collagen.

2. The method of claim 1 further comprising retracing said centrifugal corneal incision with said blade.

3. The method of claim 1 wherein said vibrating blade has a diamond front and reverse cutting edge.

4. The method of claim 1 wherein said vibrating blade is attached to a vibrating blade handle thereby causing said blade to vibrate.

5. The method of claim 1 conducted by laterally or coaxially vibrating said blade.

6. The method of claim 1 conducted by ultrasonically vibrating said blade.

7. The method of claim 1 employing a 200–215 u reverse-edge cutting blade for squaring-off the corneal incision at the optical zone.

* * * * *